United States Patent
Sutton

(10) Patent No.: US 7,247,746 B2
(45) Date of Patent: Jul. 24, 2007

(54) CRYSTAL FORMS OF N-(TRANS-4-ISOPROPYLCYCLOHEXYL CARBONYL)-D-PHENYLALANINE

(75) Inventor: Paul Allen Sutton, Parsippany, NJ (US)

(73) Assignee: Novartis, AG, Basel (CH)

( * ) Notice: Subject to any disclaimer, the term of this patent is extended or adjusted under 35 U.S.C. 154(b) by 266 days.

(21) Appl. No.: 10/510,927

(22) PCT Filed: Apr. 14, 2003

(86) PCT No.: PCT/EP03/03864

§ 371 (c)(1),
(2), (4) Date: Nov. 2, 2004

(87) PCT Pub. No.: WO03/087038

PCT Pub. Date: Oct. 23, 2003

(65) Prior Publication Data

US 2005/0256336 A1      Nov. 17, 2005

Related U.S. Application Data

(60) Provisional application No. 60/372,625, filed on Apr. 15, 2002.

(51) Int. Cl.
*C07C 229/46* (2006.01)
*C07C 235/82* (2006.01)

(52) U.S. Cl. .................. 562/450; 562/444; 562/445

(58) Field of Classification Search ................ 562/450, 562/444, 445
See application file for complete search history.

(56) References Cited

U.S. PATENT DOCUMENTS 5,463,116 A     10/1995   Sumikawa et al. ......... 562/450

FOREIGN PATENT DOCUMENTS

WO      WO 03/022251       3/2003

OTHER PUBLICATIONS

Gang, Guo-qiang, Qun-wei and Chong-quan, "A New Crystal Form of Nateglinide", *Acta Pharmaceutica Sinica*, vol. 36, No. 7, pp. 532-534 (2001).

*Primary Examiner*—Rosalynd Keys
(74) *Attorney, Agent, or Firm*—Mark W. Milstead

(57) ABSTRACT

New crystal forms of N-(trans-4-isopropylcyclohexylcarbonyl)-D-phenylalanine, also known asnateglinide, may be produced by dissolving nateglinide in any of its forms, including solvates, in an organic solvent to form a solution followed by precipitation of nateglinide from the solution, and isolating and drying the precipitated crystal form of nateglinide. The precipitation of nateglinide may be induced either by cooling the solution, or by addition of another solvent which is miscible with the first solvent but in which nateglinide is only poorly soluble, or by combination of the two. Depending on the solvent a specific crystal form of nateglinide may be obtained, e.g., the R'-type crystal form of nateglinide produced by the described method has a different melting point, infra red spectra and X-ray diffraction patterns from the previously known crystal forms of nateglinide.

7 Claims, 1 Drawing Sheet

CRYSTAL FORMS OF N-(TRANS-4-ISOPROPYLCYCLOHEXYL CARBONYL)-D-PHENYLALANINE

The present invention relates to methods for the production of different crystal forms of N-(trans-4-isopropylcyclohexylcarbonyl)-D-phenylalanine, also known as nateglinide. In particular, the invention relates to forming crystals of nateglinide referred to herein as the R'-type crystals or crystal form of nateglinide.

Nateglinide of formula (I) is a known substance having therapeutic utility in depressing blood glucose levels.

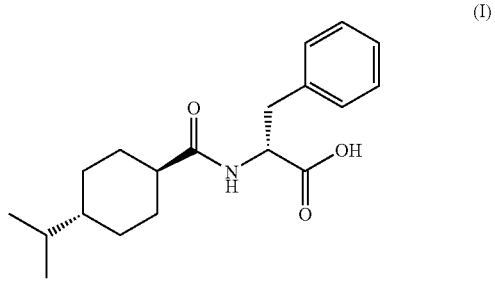

(I)

Nateglinide is disclosed in U.S. Pat. No. 4,816,484, the entire contents of which are expressly incorporated herein by reference.

Nateglinide is known to have several crystal forms. Examples of such crystal forms include the forms known as B-type and H-type crystals. The B-type and H-type crystals and methods for their production are described in U.S. Pat. No. 5,463,116, the entire contents of which are incorporated herein by reference.

According to one aspect of the instant invention herein is provided a method for the production of different crystal forms of nateglinide wherein the method comprises dissolving nateglinide in any of its forms, including solvates such as hydrates, methanolates, ethanolates and acetonates, in a solvent including mixed solvents, forming the nateglinide crystals, isolating and drying the precipitated crystal form of nateglinide.

In one embodiment of the instant invention, R'-type crystal form of nateglinide can be produced by a method wherein the method comprises dissolving nateglinide in a solvent in which nateglinide is readily soluble at an ambient temperature to form a solution, treating the solution with another solvent which is miscible with the first solvent, and in which nateglinide is only poorly soluble to induce precipitation of the R'-type crystals of nateglinide, isolating and drying the precipitated crystal form of nateglinide, including solvates such as hydrates, methanolates, ethanolates and acetonates.

Other objects, features, advantages and aspects of the present invention will become apparent to those skilled in the art from the following description, appended claims and accompanying drawings. It should be understood, however, that the following description, appended claims, drawings and a specific example, while indicating a preferred embodiment of the invention, are given by way of illustration only. Various changes and modifications within the spirit and scope of the disclosed invention will become readily apparent to those skilled in the art from reading the following.

BREIF DESCRIPTION OF DRAWINGS

As indicated, one embodiment of the instant invention provides nateglinide in R'-type crystal form. Examples of the physical properties of the B-type and the R'-type crystal form of nateglinide are as follows:

The melting point (mp) of B-type nateglinide crystals has been measured by the DSC method to be in the range of 128 to 131° C.

An example of a melting point of the R'-type crystal form of nateglinide as measured by the DSC method has been found to be about 108° C.

Figure 1:
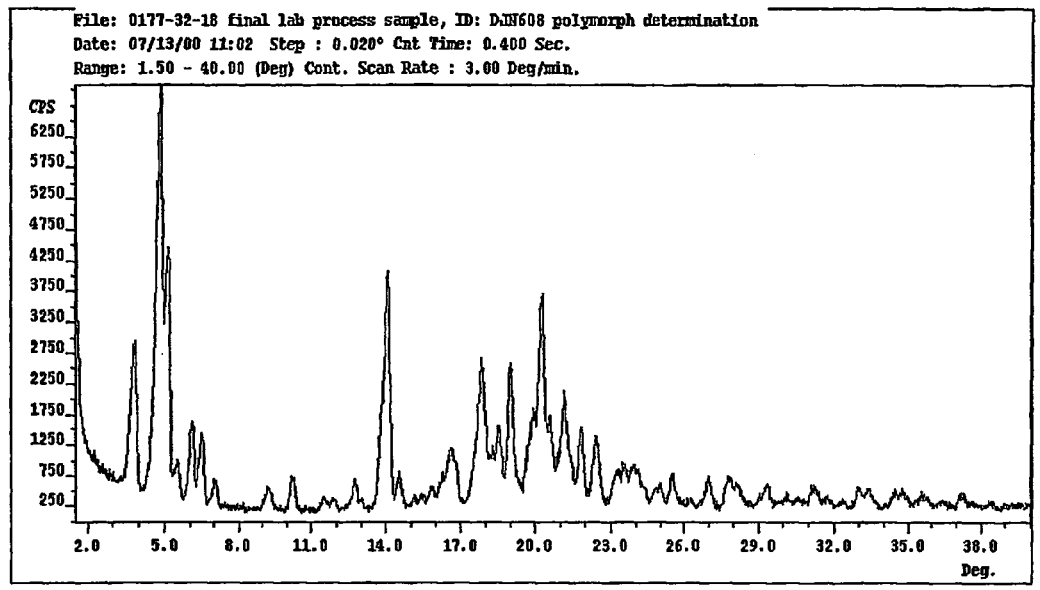
FIG. 1 shows a powder X-ray diffraction pattern of B-type crystals of N-(trans-4-isopropyl-cyclohexylcarbonyl)-D-phenylalanine.

An example of the powder X-ray diffraction patterns of the B-type crystal form of nateglinide may be found in FIG. 1. The diffraction pattern of the B-type crystal form of nateglinide shows maxima at 2θ values of 3.9, 5.0, 5.2 and 14.1.

Figure 2:
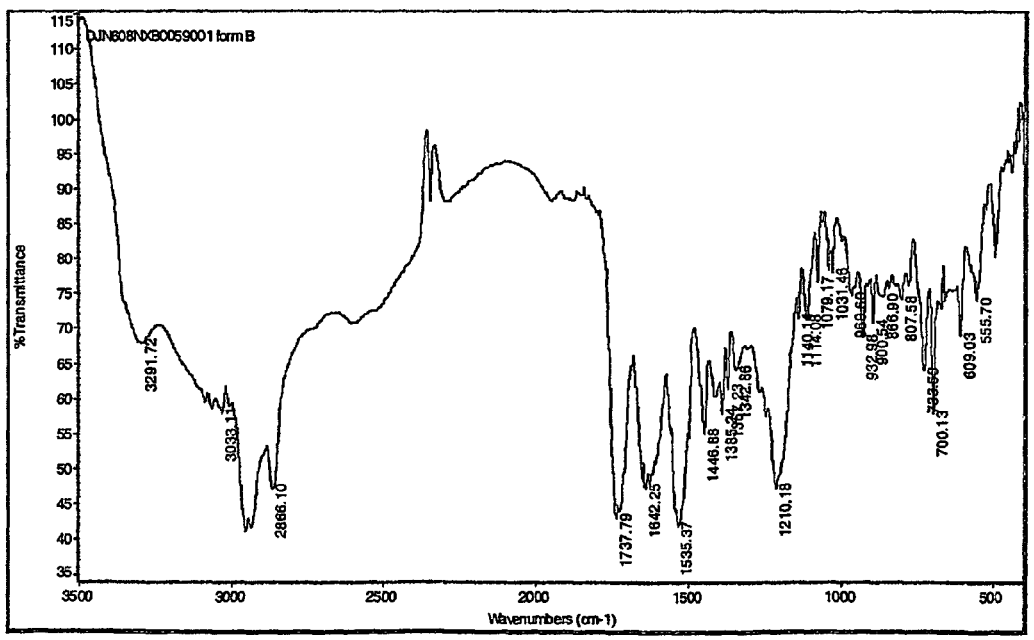
FIG. 2 shows an infra red absorption spectrum of B-type crystals of N-(trans-4-isopropyl-cyclohexylcarbonyl)-D-phenylalanine.

An example of an infrared absorption spectrum of B-type crystal form of nateglinide, obtained by a KBr method is shown in FIG. 2. The infrared absorption spectrum of the B-type crystal form of nateglinide is characterized by absorptions at around 3291, 2955, 1737, 1642 and 1210 cm$^{-1}$.

As summarized above, one aspect of the instant invention provides a method for the production of different crystal forms of nateglinide wherein the method comprises dissolving nateglinide in any of its forms, including solvates such as hydrates, methanolates, ethanolates and acetonates, in a solvent which includes mixed solvents, forming the nateglinide crystals, isolating and drying the precipitated crystal form of nateglinide.

In one embodiment, R'-type crystal form of nateglinide can be produced by a method wherein the method comprises dissolving nateglinide in a solvent, referred to herein as a first solvent, in which nateglinide is readily soluble at an ambient temperature to form a solution, treating the solution with another solvent, referred to herein as a second solvent, which is miscible with the first solvent and in which nateglinide is only poorly soluble, to induce precipitation of the R'-type crystals of nateglinide, isolating and drying the precipitated crystal form of nateglinide, including solvates such as hydrates, methanolates, ethanolates and acetonates.

First solvents in which nateglinide is readily soluble, i.e., in amounts of at least 1% by weight at an ambient temperature, include lower alcohols, such as methanol, ethanol and isopropanol. Polar solvents such as acetone, tetrahydrofuran, dioxane and dichloromethane can also be effective when used as the first solvent. Second solvents in which nateglinide is only poorly soluble, i.e., in amounts of 0.01% by weight or less, include water, hexane, heptane and diethyl ether. Where a mixed solvent is employed as the first solvent, a mixture of ethanol and toluene or a mixture of methanol and ethyl acetate is effective preferably in combination with water as the second solvent, and more preferably with water containing from about 0.5 to about 3% by weight of hydroxypropylmethylcellulose. The amount of nateglinide in the solvent ranges preferably from 1 to 50% by weight of the resulting mixture. If the amount of nateglinide is more than 50% by weight then the slurry properties of the initial suspension are poor and it will be difficult to agitate the mixture and dissolve the solid. On the other hand, it is not efficient in terms of the volume of the solvent required to use less than 1% of nateglinide by weight. The ambient temperature, i.e., the temperature in which nateglinide is dissolved in the first solvent, ranges preferably from room temperature to about the boiling point of the solvent, and more preferably from room temperature to about 70° C. The amount of nateglinide dissolved in the first solvent ranges preferably from 5 to 40% by weight of the resulting solution. The solution of nateglinide in the first solvent may be added to the second solvent, or the second solvent may be added to the solution of nateglinide in the first solvent. The ratio of the first solvent to the second solvent in the resulting mixture ranges preferably from about 1 to 3 to about 1 to 9 by volume. It may be advantageous to add seed crystals, preferably B-type nateglinide seed crystals, in the mixture to aid precipitation of the desired crystal form of nateglinide. The resulting mixture containing nateglinide may be stirred or cooled to a lower temperature for a time sufficient to assure complete precipitation of the desired nateglinide crystals.

Conventional methods, such as heating and stirring, may be used for dissolution of nateglinide. Nateglinide in any of its forms, including solvates such as hydrates, methanolates, ethanolates and acetonates, may be added to the solvent or the solvent may be added onto nateglinide, stirred, and heated to an ambient temperature ranging from room temperature to about the boiling point of the solvent to form a solution. Stirring, cooling and addition of seed crystals may be used to further induce precipitation of the desired crystal form of nateglinide. The precipitated crystals may be isolated by conventional methods, such as vacuum filtration or centrifugation. The crystals may be washed, preferably with a solvent or a solvent mixture consisting of solvents used in the crystallization. During isolation and washing, cooling may be applied, if so desired, preferably cooling the crystals to a temperature ranging from about 20 to about 0° C. The isolated nateglinide crystals may be dried under atmospheric or reduced pressure, preferably under reduced pressure ranging from about 20 to about 0.1 mmHg, at a temperature ranging from room temperature to about 80° C.

In another aspect, the present invention provides a pharmaceutical composition comprising crystals as obtainable by the above method, in particular the R'-type crystals, and pharmaceutically acceptable excipients, diluents or carriers thereof.

In a further aspect, the present invention provides a method for manufacture of a pharmaceutical composition comprising mixing an effective amount of crystals as obtainable by the method of the first aspect of the present invention, in particular the R'-type crystals, and pharmaceutically acceptable excipients, diluents or carriers thereof.

In a still further aspect, the present invention provides a method for treatment of a human or another mammal to depress its blood glucose level comprising administering an effective amount of nateglinide crystals as obtainable by the method of the present invention, in particular the R'-type crystal form.

The present invention is further described by the following example. The example is provided solely to illustrate the invention by reference to specific embodiment. This example, while illustrating certain specific aspects of the invention, do not portray the limitations or circumscribe the scope of the disclosed invention.

EXAMPLE

The R'-type nateglinide crystals may be prepared as follows:

The H-type nateglinide crystals are dissolved in a mixture of ethanol and toluene (50% of ethanol and 50% of toluene by volume; 160 mg of nateglinide/mL) at room temperature while stirring. After all the solids are dissolved, water containing 1% hydroxypropylmethylcellulose is added to induce precipitation (about 7× the volume of ethanol-toluene used). After stirring for 2 h further, the precipitated solids are collected by vacuum filtration, washed and dried overnight at 50° C. under reduced pressure to afford the R'-type crystals: mp 108° C.

Although the present invention has been described in considerable detail with reference to certain preferred versions thereof, other versions are possible without departing from the spirit and scope of the preferred versions contained herein. All references and Patents (U.S. and others) referred to herein are hereby incorporated by reference in their entirety as if set forth in full herein.

What is claimed is:

1. A method for the production of crystal form of nateglinide, comprising:
   (a) dissolving nateglinide in any of its forms in a first solvent in which nateglinide is readily soluble at an ambient temperature to form a solution, wherein the first solvent is a mixture of ethanol and toluene or a mixture of methanol and ethyl acetate;
   (b) treating the solution with a second solvent which is miscible with the first solvent, and in which nateglinide is only poorly soluble to induce precipitation of crystals of nateglinide, wherein the second solvent is water containing about 0.5 to about 3% by weight of hydroxypropylmethylcellulose; and
   (c) isolating and drying the precipitated crystal form of nateglinide.

2. The method of claim 1, wherein the precipitation of the crystal form of nateglinide is induced by stirring, cooling or by adding seed crystals of nateglinide.

3. The method of claim 1, wherein the ambient temperature ranges from room temperature to the boiling point of the solvent.

4. The method of claim 1, wherein the crystal form of nateglinide is dried under atmospheric or reduced pressure at a temperature ranging from room temperature to 70° C.

5. The method of claim 1, wherein the first solvent is a mixture of ethanol and toluene;

6. The method of claim 1, wherein the first solvent contains 50% of ethanol by volume; the second solvent contains 1% of hydroxypropylmethylcellulose; and the ratio of the first solvent to the second solvent is 1 to 7 by volume.

7. The method of claim 6, wherein the ambient temperature is room temperature; and the crystal form of nateglinide is dried under reduced pressure at a temperature ranging from room temperature to 50° C.

* * * * *